United States Patent [19]
Rose

[11] Patent Number: 5,587,532
[45] Date of Patent: Dec. 24, 1996

[54] METHOD OF MEASURING CRACK PROPAGATION IN OPAQUE MATERIALS

[75] Inventor: Douglas N. Rose, Macomb County, Mich.

[73] Assignee: The United States of America as represented by the Secretary of the Army, Washington, D.C.

[21] Appl. No.: 371,719

[22] Filed: Jan. 12, 1995

[51] Int. Cl.$^6$ .................................................. G01N 29/04
[52] U.S. Cl. .................................................. 73/579; 73/571
[58] Field of Search .......................... 73/571, 587, 606, 73/643; 250/492.1, 492.2, 492.3; 374/5; 356/432

[56] References Cited

U.S. PATENT DOCUMENTS

| | | | |
|---|---|---|---|
| 4,028,932 | 6/1977 | Rosencwaig | 73/579 |
| 4,267,732 | 5/1981 | Quate | 73/606 |
| 4,543,486 | 9/1985 | Rose | 73/606 |
| 4,562,736 | 1/1986 | Iwasaki | 73/587 |

*Primary Examiner*—Hezron E. Williams
*Assistant Examiner*—Christine K. Oda
*Attorney, Agent, or Firm*—Peter A. Taucher; Gail S. Soderling

[57] ABSTRACT

A microscopy-thermal wave microscopy apparatus for measuring crack propagation resistance based on the lateral crack system induced by forming a hardness indentation in an opaque material the resistance and crack extent providing a quantitative measure of the spalling propensity of the opaque material.

1 Claim, 1 Drawing Sheet

METHOD OF MEASURING CRACK PROPAGATION IN OPAQUE MATERIALS

GOVERNMENT INTEREST

The invention described herein may be manufactured, used and licensed by or for the Government for governmental purposes without payment to me of any royalty.

BACKGROUND OF THE INVENTION

1. Field of the Invention

In one aspect this invention relates to a method of testing ceramic materials. In yet a further aspect, this invention relates to a method to predict and rank the abrasion characteristics of ceramic materials. In still a further aspect, this invention relates to an apparatus for measuring subsurface cracks in opaque ceramic materials. In yet a further aspect this invention relates to the machining characteristics of ceramic materials.

2. Prior Art

Advanced ceramics are useful in a wide variety of wear applications. Some examples are bearings in automotive valve trains and high speed machine tools. The general physical properties of ceramics, such as strength and hardness, are easily measured; however, these properties do not correlate well with the actual bearing performance or machining characteristics of the materials. Lack of a reliable technique for predicting abrasion performance requires each ceramic to be extensively tested under actual operating conditions. This is expensive and time consuming for each material and many inappropriate materials will be tested further increasing costs. Also the time consumed testing unsuitable materials will increase the time until acceptable materials are found for a given application.

A more reliable analysis tool than simply ranking materials by physical properties such as strength is needed for predicting a ceramic material's wear resistance.

It is generally observed that ceramic bearings fail by spalling on the bearing surface. Since spalling is the apparent failure mode, a method for viewing the spalling pattern would provide an improved provide an improved ability to predict and rank the performance of ceramic materials.

The spalling failure mechanism is closely tied to the formation of subsurface lateral cracks in the material, and subsequent propagation of the subsurface lateral crack until a chip falls from the surface. Thus, a technique for investigating the initiation and propagation of lateral cracks in a ceramic will provide an improved means of rating ceramics for wear resistance. The fracture toughness of a ceramic is related to the crack length produced by a defined force causing an indentation.

Because most ceramics suitable for industrial use are opaque and have poor electrical conductivity there was no reliable technique for studying subsurface phenomena since conventional optical and electrical techniques were unavailable.

BRIEF SUMMARY OF THE INVENTION

I have developed a novel technique for studying lateral crack structure in opaque ceramics which will work even when the cracks measure on the order of 0.5 mm and smaller and have linked those requirements with ceramic performance in wear applications.

Briefly, a thermal imaging method is proposed which allows imaging of subsurface lateral cracks in fine detail in opaque ceramic materials. Also disclosed is an apparatus for carrying out the technique. The technique can also be used to measure crack propagation resistance based on lateral crack formation under different conditions. Although the present discussion is focused on ceramic materials the concept can be applied to studying subsurface defects in other opaque materials.

Broadly the method of this invention starts with the formation of a subsurface crack in the material using a pointed indentor of a known load. Then a modulated beam is moved across the surface of the test specimen to generate alternate heating and cooling. The temperature changes in the material caused by the alternate heating and cooling cause a physical phenomena near the heated area which will be effected by the presence of a crack indicating both the presence of a crack and its location with respect to the surface.

One apparatus useful in the present invention uses a photoacoustic device to measure changes in gas temperature at the ceramic surface as acoustic waves indicating the presence of a subsurface crack and its size with a high degree of resolution.

DETAILED DESCRIPTION OF PREFERRED EMBODIMENTS

Figure 3:
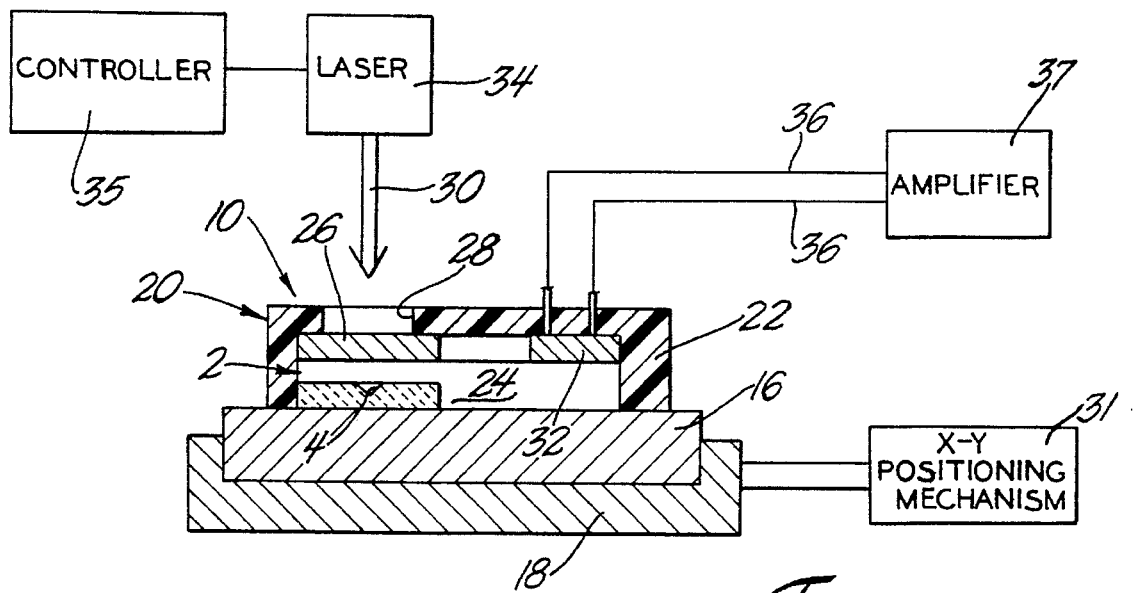
FIG. 3. is a schematic representation of one apparatus useful in the practice of this invention.

The ceramics to be tested using the present technique are generally opaque to light. Some representative materials include silicon nitride, silicon carbide, titanium carbide, titanium nitride, tantalum nitride, tantalum carbide, alumina as well as other opaque ceramic materials.

The technique is also useful in studying mixtures, composites and laminates of these materials. In the case of layered components, the test conditions can be varied based on the thickness of the lamina in which the indention is being made to provide a new and unique method of testing the strength of the bond between two or more lamella. Composite structures are very common in coated cutting tool structures where thin ceramic coatings are applied in order to enhance the tool properties by combining the toughness of one material with the abrasion resistance or other desired machining property of a second ceramic.

The first step in testing a ceramic material's crack initiation and propagation properties using the method of this invention is to form an indentation in the surface of the ceramic to be tested. One of the best known procedures for forming surface indentations is to use a diamond indentor pressed into the surface using a known load. Two of the most common diamond shaped indentor tests are the Knoop and Vickers hardness tests. The Vickers hardness tester uses a symmetrical pyramid structure which results in a surface indentation with equal length axes while the Knoop indenter uses an elongated pyramidal point which forms an elongated indention with one long and one short axis.

Either tester gives an indentation which can be used in the practice of this invention. The Knoop indentor gives a longer trace to measure on hard materials and it also tends to sample the hardness close to the surface better than the Vickers test which penetrates further into the material for a given surface trace length. The equipment and indentors are standard hardness testing equipment and further discussion is omitted in the interest of brevity. One skilled in the art can choose the appropriate indentor to fulfil their requirements based on material hardness and the indentation to be formed. The impressions discussed in this application were made using standard equipment and techniques.

The advantages of using the standard techniques includes 1) only a routine hardness tester is needed; 2) the indentation has a well defined geometric pattern which can be accurately positioned; and 3) the indentation is readily controlled to a high degree of reproducibility by means of the contact load. Also the tests require only a rather small polished area on a sample to make several indentations and tests. Because of the small area used, the tests can be run on a small area of actual parts obviating the need for sample pieces and further allowing the testing of actual production run ceramic parts.

The loads, used to make the indentations, that is the force applied to the indenter can be varied; the general range of loads useful in the practice of this invention are on the order of 2 to 50 kilograms more specifically 10 to 30 kilograms. The loads used will determine the force applied to the indenter and consequently the depth or penetration of the indention. The load may need to be varied for different types of ceramic materials since the penetration and resulting indention are related to the hardness of the material with the harder materials requiring a higher load to get a good indentation. In practicing the present invention, the load must be large enough to result in a subsurface lateral crack in the ceramic after the indenter load has been released; therefore, the loads will frequently be higher than those used solely for hardness testing since a crack must be propagated. A number of indentations can be made varying the load to produce cracks of various sizes and provide a measure of the load a which a crack will be initiated and the propagation rate of a crack to be expected when a crack has been initiated.

Various beams can be used to generate a temperature increase on the ceramic surface in practicing this invention. Examples of suitable beams include lasers, microwaves, x-rays, ion particle beams and electrons. The beam can be chosen based on the degree of heating desired and the degree of modulation desired to image the subsurface crack. All of the beams mentioned as well as other types of particle beams and electromagnetic radiation, e.g., infrared, ultraviolet, and gamma radiation will serve to heat the ceramic surface above a subsurface crack.

The particular beam chosen for use in this invention will be modulated when being used to image a subsurface crack. The beam can be pulsed by means of a modulating circuit controlling the beam's power causing a pulsed power beam. The beam can also be mechanically interrupted such as by the use of a rotating disk with one or more slots interposed in the beam path to provide a pulsed beam. The modulation frequency will be dependant on the pickup device used since the modulation rate has to be compatible with the pickup's sensitivity and response time.

Examples of suitable sensors or pick up means are, the microphones used in hearing aids. When an acoustical pickup or other audio device is used as a sensing means, the modulation will be in the normal audio range of 1 to 20 KHz since these are the frequencies sensed by such devices. The modulation frequency chosen will determine the degree of resolution possible and depth below the ceramic surface of measurement. When the modulation is at a high frequency, short energy bursts, periodic surface heating is confined to the material near the surface so only cracks near the surface will be detected and imaged while lower frequency modulation, longer energy bursts, will provide greater energy which periodically heats the, material deeper allowing imaging of deeper cracks.

The frequency and depth of heating does however effect the resolution of the process. Where the beam heats the material to a depth of about 0.02 mm the process will resolve cracks of up to about 0.02 mm in length. When the material is heated to a depth of about 0.1 mm the process will resolve cracks below the surface only up to about 0.1 mm long. Thus it is necessary to consider the size of the crack and its probable depth in the material when determining the test conditions to be used and interpreting the results. Of course it would be possible to make multiple passes of a particular indentation at various modulations in order to get a determination of crack size and its location in the ceramic.

One specific example, of a useable beam is a CW Argon ion laser which has the capacity to provide a power density of about 1–10 KW/cm$^2$ over a small area on a ceramic surface. When the beam modulation is controlled to provide power pulses of 10 to 100 milliseconds, surface temperatures up to 1000 to 1600 C. can result.

Figure 1:
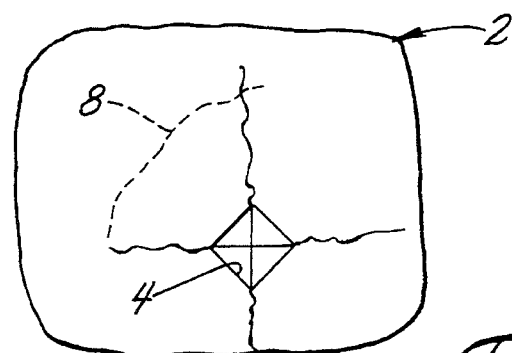
FIG. 1. is a top view of an opaque ceramic material with a Vickers indention and a subsurface crack.
Figure 2:
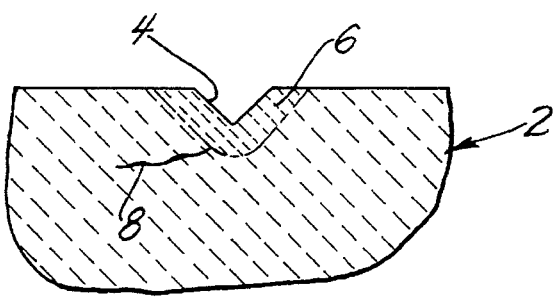
FIG. 2. is a side view in section of the FIG. 1 taken along the line 2—2.

By way of background, reference is made to the drawing and initially to FIGS. 1 and 2, a block of ceramic material 2 has a Vickers indentation 4 formed on the top surface. This indentation will strongly deform the material under the indentor forming a plastic deformation zone 6, shown in FIG. 2. A subsurface crack 8 will be propagated and emanate from the plastic deformation zone. As shown most clearly in FIG. 2 the subsurface crack can be completely contained within the ceramic; thus, the crack can not be measured using optical techniques when the ceramic is opaque. The indentation also generates vertical cracks 9 which extend outward from the corners of the indentation. The vertical cracks are visible on the surface and extend into the material dividing the subsurface crack zone into quadrants.

FIG. 3 shows one possible detection apparatus according to this invention. The apparatus designated generally 10 can be described generically as a gas cell detector using a laser as the heat source. In FIG. 3, a gas cell structure 20 is mounted on the base block 16 surrounding the ceramic sample 2. The gas cell has a housing 22 with one open side mounted on a base block 16 so as to form a gas tight chamber 24 within the housing. The housing 22 has a sealed transparent window 26 mounted in an aperture 28 formed in its upper surface which allows a modulated beam of radiation 30 to strike the upper surface of the sample 2 being tested. Generally the gas cell 22 is smaller than the material 2 being tested so it will be mounted on the surface surrounding and enclosing any indents. During testing the x-y platform 18 is moved in a predetermined pattern by means of an x-y positioning mechanism 31. Such x-y positioning mechanisms are a well known laboratory mechanism and a detailed description is omitted in the interest of brevity. The x-y mechanism should be moveable in small increments on the order of 0.10 mm to allow accurate positioning.

A number of different discrete points on the ceramic test specimen 2 about the indentation 4 in the sample being tested, would be heated using the beam. When constructing the gas cell 20 it is desirable to minimize the volume of chamber 24 in order to minimize the gas volume. This will lower the volume of gas to be heated during testing providing a better signal to noise ratio for the test apparatus 10 though the window needs to be a couple of thermal diffusion lengths from the surface.

The perimeter of the housing 22 will be sealed to the base block by means of a suitable sealant. One class of suitable sealants are waxes which provide a good seal to isolate the gas within the chamber from outside disturbances. Silicone compounds could also be used as sealants particularly when it is not necessary to remove the sealant after testing. When testing is being carried out on production parts which will be used later in the intended application water soluble glues.

A microphone 32 is mounted in the housing 22 in fluid communication with the chamber 24 so as to receive the acoustic signals generated by changes in gas pressure within the chamber. Numerous small microphones are available and could be used in practicing this invention. For example, normal hearing aid microphones are capable of sensing the gas pressure variations produced in a closed cell such as that shown in the FIG 3. The signal detected by the microphone is usually small and the resulting signal will be amplified to provide a more pronounced signal.

In FIG. 3, a beam 30 generated by a laser 34 is directed as a stream of radiation on to the sample 2 surface through the transparent window 26 contained in the housing 22. The beam 30 is modulated by a control means 35, such beam modulators being known in the art. The beam in provides a series of radiation pulses of a definite duration to the surface of the sample 2. The radiation striking the surface is absorbed heating the surface which in turn heats the gas in contact with the ceramic surface. The heating of the gas creates a pressure wave within the chamber which can be sensed by the microphone 32 and the resulting electrical signal is sent to an amplifier 32 via leads 36. The amplified signal can be sent to a recorder or other device for analysis and storage.

The microphone 32 will generate an electrical signal proportional to the pressure changes in the gas. Where there is a crack in the ceramic, the heat generated at the ceramic surface will be hindered from flowing away from the surface creating greater pressure changes indicating the existence of a crack under the surface of the ceramic.

The acoustic signal generated at the ceramic surface will have two separate and distinct characteristics, that is, magnitude and phase. The incident beam will be uniformly phased. However, the output will depend on the existence or nonexistence of a crack. Where there is no crack there will be little or no modification of the phase while where there is a crack the heat will be unable to diffuse into the ceramic and the phase will shift from its value over an the undamaged area. The closer to the surface the crack, the sooner the heat will stop its diffusion into the ceramic. Thus the modification of the phase will provide an indication of a crack and its depth.

The presence of a crack will also effect the magnitude of the acoustical wave generated. As noted above, the presence of a crack will hinder the diffusion of heat into the ceramic and the depth of the crack will determine how much heat can be dissipated effecting the size of the temperature differential created by the beam and therefore the magnitude of the response generated.

As a working example, hot pressed silicon nitride ($Si_3N_4$) blocks (NC132 from Norton Co.) were metallographicly polished and a Vickers indentor used to impress indentions into the surface of the blocks at loads of 2, 5, 10, 15, 20, 25 and 30 Kg. These loads may exceed those normally used for hardness testing but they were chosen to ensure the propagation of cracks in the ceramic for measurement and testing.

The microstructure of this particular $Si_3N_4$ material is predominantly beta material grains with a 1–2 μm diameter and a 10–15 μm length. The grains are preferentially oriented perpendicular to the pressing direction so they lie in the plane of the images shown by FIGS. 1 and 2. Radial cracks emanating from the indentation will thus tend to cross the grains but the lateral cracks of interest will tend to propagate parallel to the grains below the surface as shown in FIG. 2.

The 20 Kg indents were analyzed in greater detail. An apparatus like that shown in FIG. 3 with an argon laser described above as a heat source was passed over the indent region. The laser has a focal spot of 8.1 μm and the focal spot was moved in 4.0 μm increments when imaging 20 Kg indents in a grid pattern about the indentation. The frequency of the laser was varied form 175 to 10,000 hertz. The area scanned measured about 1.53 mm by 0.508 mm.

The photoacoustic pick up showed a crack formation with a smaller diameter at the higher frequencies, shallower heating, and a larger diameter crack pattern at the lower frequencies, deeper heating. This implies the cracks made by the indentor are shallower at the indent and move downward into the material as the crack propagates away from the indent. Similar analysis of the crack system made by the indentor using loads other than 20 Kg showed that the cracks in the $Si_3N_4$ began at the indent and sloped deeper into the material with a flattening out at the extremities of the crack as a general rule. The heavier loads produced cracks deeper into the $Si_3N_4$ material as would normally be expected.

$Si_3N_4$ material of a different structure normally used in engine application and manufactured by Coors ceramic have been examined after being subjected to a number of cyclic fatigue by repeatedly impressing a ball onto the surface of the ceramic to simulate the repetitive high cycle lower stress patterns normally encountered in internal combustion engines where the material is not subjected to individual forces sufficient to initiate cracks but the cumulative effect results in spalling. Examination using the technique above shows there is material property change below the surface before any spalling or other visible surface degradation become visible.

It is apparent from the foregoing description that an apparatus and method for locating, and measuring subsurface lateral cracks in opaque ceramic materials has been disclosed. Various modifications and alterations will become apparent to those skilled in the art with out departing from the scope and spirit of this invention and it is understood that this invention is not limited to the illustrative embodiments set forth above.

What is claimed is:

1. A method of testing the susceptibility of an opaque ceramic material to failure by spalling comprising the steps of:

making a series of impressions using a pointed indentor at different loads in the surface of the opaque ceramic to be studied to form a sample;

mounting the impressed sample on a base with the surface containing the impressions exposed;

enclosing the sample within a housing and sealing the housing to the base to form a chamber, the housing having a transparent window through which radiation passes;

exposing the surface of the sample with the indentations to a modulated beam of radiation in a predefined pattern about the impressions using different degrees of beam modulation to alternately heat and cool a small defined portion of the exposed surface;

measuring the magnitude of the pressure waves generated by the alternate heating and cooling;

analyzing the difference in the pressure wave magnitude produced by the alternate heating and cooling as a function of the modulation of the radiation beam to determine the depth and size of the subsurface radial cracks formed by the indentor within the opaque ceramic;

whereby the subsurface radial crack formation is disclosed which correlates to the spalling susceptibility of the opaque ceramic.

* * * * *